(12) United States Patent
Lui et al.

(10) Patent No.: US 9,656,966 B2
(45) Date of Patent: May 23, 2017

(54) METHOD FOR PREPARING 1-ALKYL-3-DIFLUOROMETHYL-5-FLUOR-1H-PYRAZOLE-4-CARBALDEHYDES AND 1-ALKYL-3-DIFLUOROMETHYL-5-FLUOR-1H-PYRAZOLE-4-CARBOXYLATES

(71) Applicant: BAYER CROPSCIENCE AKTIENGESELLSCHAFT, Monheim am Rhein (DE)

(72) Inventors: Norbert Lui, Odenthal (DE); Sergii Pazenok, Solingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/113,377

(22) PCT Filed: Jan. 22, 2015

(86) PCT No.: PCT/EP2015/051184
§ 371 (c)(1),
(2) Date: Jul. 21, 2016

(87) PCT Pub. No.: WO2015/110493
PCT Pub. Date: Jul. 30, 2015

(65) Prior Publication Data
US 2017/0008852 A1 Jan. 12, 2017

(30) Foreign Application Priority Data
Jan. 24, 2014 (EP) .................................. 14356001

(51) Int. Cl.
*C07D 231/16* (2006.01)
(52) U.S. Cl.
CPC ................... *C07D 231/16* (2013.01)
(58) Field of Classification Search
None
See application file for complete search history.

(56) References Cited

U.S. PATENT DOCUMENTS

| 8,431,718 B2 | 4/2013 | Pazenok et al. | 548/374.1 |
| 8,436,191 B2 * | 5/2013 | Pazenok | C07D 231/16 548/366.1 |
| 2006/0122399 A1 | 6/2006 | Gonzalez et al. | 548/200 |
| 2007/0043220 A1 | 2/2007 | Conner et al. | 548/376.1 |
| 2011/0207940 A1 | 8/2011 | Pazenok et al. | 548/366.1 |
| 2011/0288305 A1 | 11/2011 | Pazenok et al. | 548/374.1 |
| 2013/0123510 A1 | 5/2013 | Braun et al. | 548/374.1 |
| 2013/0165664 A1 | 6/2013 | Pazenok et al. | 548/366.1 |
| 2015/0126748 A1 | 5/2015 | Pazenok et al. | |

FOREIGN PATENT DOCUMENTS

| WO | WO 2011/131615 | 10/2001 |
| WO | WO 2004/063165 A1 | 7/2004 |
| WO | WO 2006/018725 | 2/2006 |
| WO | WO 2011/061205 A1 | 5/2011 |
| WO | WO 2012/010692 A1 | 1/2012 |
| WO | WO 2013/171134 A1 | 11/2013 |

OTHER PUBLICATIONS

Len F. Lee et al.: "Synthesis and $^{13}$C NMR of (Trifluoromethyl)hydroxypyrazoles", J. Heterocyclic Chem., vol. 27, pp. 243-245, Feb. 1990.
Bruce C. Hamper et al.: "Cyclocondensation of Alkylhydrazines and β-Substituted Acetylenic Esters: Synthesis of 3-Hydroxypyrazoles", J. Org. Chem., 1992, 57, 5680-5686.
International Search Report issued Feb. 23, 2015 in corresponding International Application No. PCT/EP2015/051184.

* cited by examiner

*Primary Examiner* — Kamal Saeed
(74) *Attorney, Agent, or Firm* — Morrison & Foerster LLP

(57) ABSTRACT

The present invention relates to a novel method for preparing 1-alkyl-3-difluoromethyl-5-fluor-1H-pyrazole-4-carbaldehydes or esters thereof of formula (I) by means of reductive dehalogenation, starting from 1-alkyl-3-chlorodifluoromethyl-5-fluoro-1H-pyrazole-4-carbaldehydes or esters thereof Formula (I)

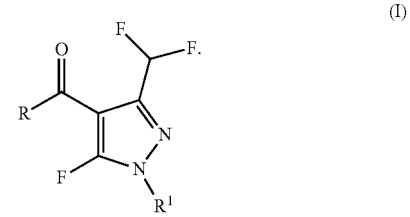

7 Claims, No Drawings

METHOD FOR PREPARING 1-ALKYL-3-DIFLUOROMETHYL-5-FLUOR-1H-PYRAZOLE-4-CARBALDEHYDES AND 1-ALKYL-3-DIFLUOROMETHYL-5-FLUOR-1H-PYRAZOLE-4-CARBOXYLATES

CROSS-REFERENCE TO RELATED APPLICATION(S)

The present application is a 35 U.S.C. §371 national phase conversion of PCT/EP2015/051184 filed on Jan. 22, 2015, which claims priority of European Application No. 14356001.9 filed on Jan. 24, 2014. Applicants claim priority to each of the foregoing patent applications. The PCT International Application was published in the English language.

FIELD OF THE INVENTION

The present invention relates to a novel method for preparing 1-alkyl-3-difluoromethyl-5-fluor-1H-pyrazole-4-carbaldehydes or esters thereof of formula (I) by means of reductive dehalogenation, starting from 1-alkyl-3-chlorodifluoromethyl-5-fluoro-1H-pyrazole-4-carbaldehydes or esters thereof of formula (II)

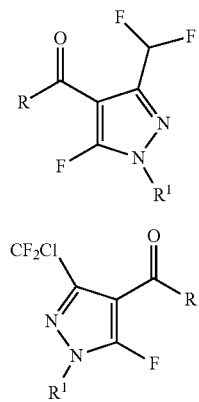

wherein $R^1$ is $C_1$-$C_6$-alkyl and R is H or $C_1$-$C_6$-alkoxy.

BACKGROUND OF THE INVENTION

1-Alkyl-3-haloalkyl-5-fluoropyrazolecarbaldehydes and esters thereof are important building blocks for preparing plant protection active ingredients, particularly SDHI fungicides.

1-Alkyl-3-difluoromethyl-5-fluor-1H-pyrazole-4-carbaldehydes was so far typically prepared in a multi-stage transformation starting from difluoromethylacetoacetate (WO 2011061205):

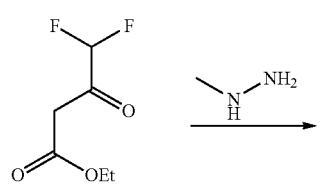

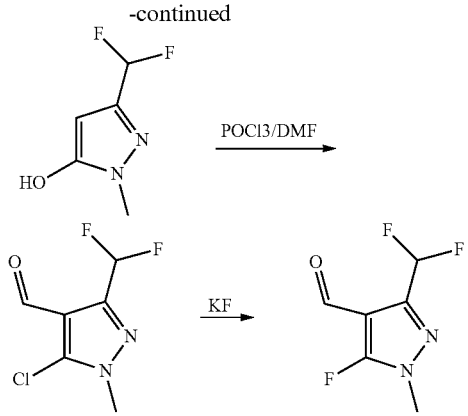

Starting material for this transformation, i.e. ethyldifluoracetoacetate, is a rather unstable compound, difficult to purify and which loses its quality during storage. This makes the utilization of this compound, especially on industrial scale, difficult.

The transformation of pyrazolic compounds bearing $CF_2H$ group is a challenging task as well, since this group is rather unstable under acidic conditions and easily releases fluoride which can damage reaction vessel, especially on a technical scale.

A process for the preparation of esters of 1-alkyl-3-fluoroalkylpyrazole-carboxylic acids via the reduction of 3-chlorodifluoromethylpyrazolic carboxylates was known from WO 2012/010692. Nevertheless, it was not known nor expected that a reductive dehalogenation of $CF_2Cl$-group can occur in pyrazoles bearing a halogen atom in position 5 or a carbaldehyde function in position 4 without undesirable effect on said halogen atom in position 5 or carbaldehyde function in position 4. On contrario, the skilled man would expect that the aldehyde group will also at least partially react, and/or that the fluorine atom in position 5 will also at least partially react, as it is shown or suggested in WO 2013/171134 and WO 2004/063165. Indeed WO 2013/171134 shows the reductive elimination of the halogen atom in position 5 of 5-chloro-1-alkyl-3-difluormethylcarbaldehyde, and WO 2004/063165 describes the removal of a chlorine atom in N-aryl-3-methyl-5-chloropyrazole-carbaldehydes.

SUMMARY OF THE INVENTION

It has now surprisingly been found that, under the conditions of the invention, it is possible to selectively remove a halogen atom from a chlorodifluoromethyl group in 1-alkyl-3-chlorodifluoromethyl-5-fluoro-1H-pyrazole-4-carbaldehydes of formula (IIa) or 1-alkyl-3-chlorodifluoromethyl-5-fluor-1H-pyrazole-4-carboxylates of formula (IIb), without affecting or reducing the fluorine atom in position 5, without reducing the carbaldehyde or carboxylate group in position 4 and without attacking the pyrazole ring.

It has also surprisingly been found that the reductive dehalogenation of 5-Fluoro-1-alkyl-3-chlorodifluoroalkyl-1H-pyrazole-4-carbaldehydes and esters thereof leads selectively and in high yield to the 1-alkyl-3-difluoromethyl-5-fluoro-1H-pyrazole-4-carbaldehydes and esters thereof.

It has now been found that 1-alkyl-3-difluoromethyl-5-fluor-1H-pyrazole-4-carbaldehydes or esters thereof of formula (I)

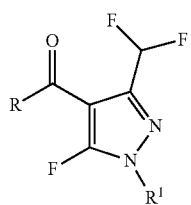

(I)

wherein $R^1$ is $C_1$-$C_6$-alkyl and R is H or $C_1$-$C_6$-alkoxy,
can be obtained by reacting 5-fluoro-1-alkyl-3-chlorodifluoromethyl-5-fluoro-1H-pyrazole-4-carbaldehydes or esters thereof of formula (II)

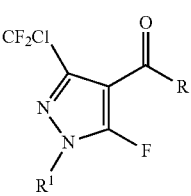

(II)

wherein R and $R^1$ are as stated above,
by means of catalytic hydrogenation and optionally in the presence of a base.

It has now been found that 1-alkyl-3-difluoromethyl-1H-pyrazole-4-carbaldehydes of formula (Ia) or 1-alkyl-3-difluoromethyl-5-fluoro-1H-pyrazole-4-carboxylates of formula (Ib)

(Ia)

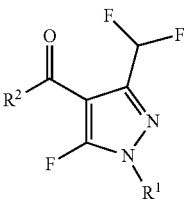

(Ib)

where $R^1$ is $C_1$-$C_6$-alkyl, and $R^2$ is $C_1$-$C_6$-alkoxy,
can be obtained by reacting 5-fluoro-1-alkyl-3-chlorodifluoromethyl-5-fluoro-1H-pyrazole-4-carbaldehydes of formula (IIa) or 1-alkyl-3-chlorodifluoromethyl-5-fluor-1H-pyrazole-4-carboxylates of formula (IIb) respectively

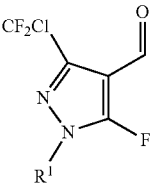

(IIa)

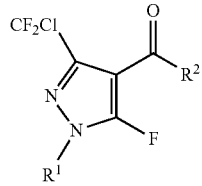

(IIb)

where $R^1$, $R^2$ have the meanings stated above,
by means of catalytic hydrogenation and optionally in the presence of a base.

DETAILED DESCRIPTION OF THE INVENTION

The method according to the invention may be illustrated by the following formula schemes:

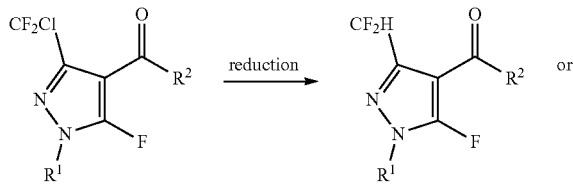

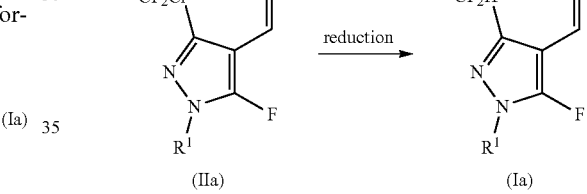

where $R^1$ is $C_1$-$C_6$-alkyl, and $R^2$ is $C_1$-$C_6$-alkoxy.

The radical $R^1$ is preferably methyl, ethyl, n-propyl, isopropyl, butyl, pentyl, particularly preferably methyl or ethyl, even more preferably methyl.

5-Fluoro-1-methyl-3-difluoromethyl-1H-pyrazole-4-carbaldehyde (II-1) or esters thereof and 5-Fluoro-1-ethyl-3-difluoromethyl-1H-pyrazole-4-carbaldehyde (II-2) or ester thereof are very particularly preferably used as starting material.

The reaction is carried out in the presence of hydrogen. It is possible to use either pure hydrogen or mixtures of hydrogen and an inert gas (up to 1:1), such as nitrogen or argon. The reaction is carried out at pressures of 1 bar to 50 bar, preferably 1 bar to 20 bar and particularly preferably 2 bar to 15 bar.

To scavenge the hydrogen chloride, formed during the reaction, a base is optionally added. As added base, either an inorganic base such as sodium carbonate, potassium carbonate, sodium bicarbonate, potassium bicarbonate, mono-, di- or trisodium phosphate or tripotassium phosphate, sodium hydroxide or potassium hydroxide or an organic base such as triethylamine, tributylamine, diazabicycloundecene (DBU), diazabicyclononene (DBN), pyridine, lutidine, 2-, 3- or 4-picoline or diazabicyclooctane (DABCO) can be used. Preference is given to the use of triethylamine 0.5 to 20 molar equivalents, preferably 0.5 to 5 molar equivalents and particularly preferably 1 to 5 molar equivalents of the base are added, based on the substrate.

In the catalytic hydrogenation for reducing the compound of the general formula (II), any hydrogenation catalyst may be used as catalyst. Suitable catalysts include optionally one or more metals from groups 8-10 of the periodic table on any conventional inorganic support. Examples include noble metal catalysts, such as ruthenium catalysts, palladium catalysts, platinum catalysts and rhodium catalysts, Raney nickel catalysts and Raney cobalt and Lindlar catalysts. In addition to these heterogeneous catalysts, hydrogenations over homogeneous catalysts can, however, also be carried out, for example over the Wilkinson catalyst. The relevant catalysts may be used in supported form, for example on carbon (charcoal or activated charcoal), aluminium oxide, silicon dioxide, zirconium dioxide, calcium carbonate or titanium dioxide. Catalysts of this kind are known per se to those skilled in the art. Particularly preferred are palladium catalysts supported on calcium carbonate. The catalysts may be used either in water-moist or in dried form. The catalyst used is preferably reused for a plurality of conversions. In the method according to the invention, the catalyst is used at a concentration of approximately 0.01 to approximately 30% by weight, based on the halo-1-alkyl-3-fluoroalkyl-1H-pyrazole-4-carbaldehyde of the formula (II) used. The catalyst is preferably used at a concentration of approximately 0.1 to approximately 5% by weight.

In the process according to the invention, the reduction is advantageously carried out in the presence of at least of one additive. Typical additives are, NH₄OAc, Sodium Acetate, MgF2, NH₄F, AlF₃, K₂CO₃, Borax. Especially K₂CO₃, NH₄Cl, NH₄F, CsF or Borax.

The reaction time may be up to 20 hours, depending on the reactivity of the reactants, while the reaction can also be terminated earlier when conversion is complete. Preference is given to reaction times of 3-10 hours.

The reaction is carried out in the presence of a solvent. Suitable solvents are: alcohols, ethyl acetate, isopropyl acetate, THF, methyltetrahydrofuran, dioxane, toluene, hexane, heptane, pentane or petroleum ether. Particular preference is given to the use of methanol, ethanol, DMSO, dimethylacetamide, DMF or NMP.

5-Fluoro-1-alkyl-3-chlorodifluoroalkyl-1H-pyrazole-4-carbaldehydes of the formula (IIa) can be prepared by known methods (cf. *J. Het. Chem.* 1990, 27, 243, WO 2006/018725 A1, WO 2011/061205 A1, B. Hamper et al. *Journal of Organic Chemistry* V.57,N21,5680-6, WO 2011061205, WO2013171134 and WO2011131615).

The preparation of compounds could be performed according to the following schema.

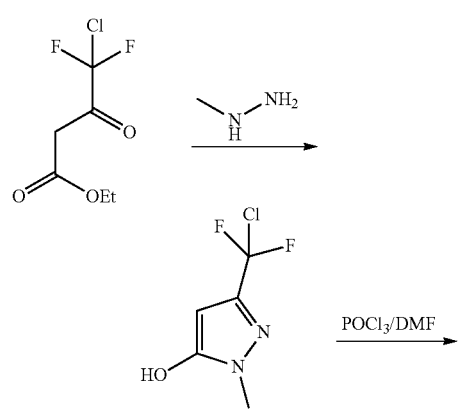

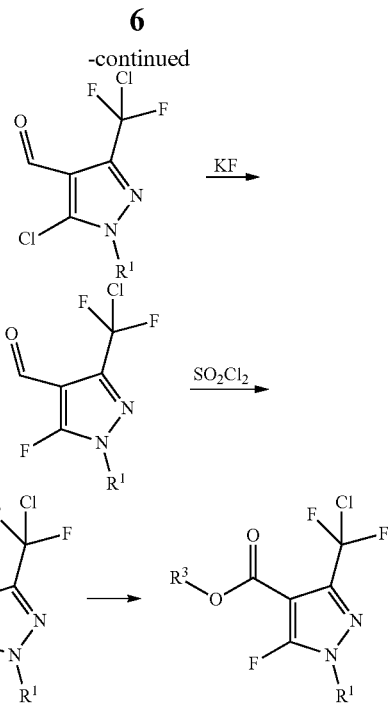

where $R^1$ and $R^3$ are independently C1-C6-alkyl.

PREPARATION EXAMPLES

Example 1

1-methyl-3-difluoromethyl-5-fluoro-1H-pyrazole-4-carbaldehyde

In an autoclave 10 g of 5-chloro-3-(difluorochlormethyl)-1-methyl-1H-pyrazole-4-carbaldehyde dissolved in 150 ml of THF and 10 g triethylamin and 500 mg of 5% palladium on calcium carbonate were added. The autoclave was flushed with nitrogen and pressurised to 15 bar hydrogen. Reaction mixture in autoclave was stirred at 90° C. for 6 h. After filtration of the catalyst, the solvent was removed under reduced pressure and the product was obtained as a solid and purified via crystallization from mixture isopropanol/water. Yield 7 g, melting point 68-69° C.

Example 2

In an autoclave 10 g of 5-chloro-3-(difluorochlormethyl)-1-methyl-1H-pyrazole-4-carbaldehyde dissolved in 150 ml of THF and 10 g CsF and 400 mg of 150 mg Pd(OH)2 on carbon were added. The autoclave was flushed with nitrogen and pressurised to 15 bar hydrogen. Reaction mixture in autoclave was stirred at 90° C. for 6 h. After filtration of the catalyst, the solvent was removed under reduced pressure and the product was obtained as a solid and purified via crystallization from mixture isopropanol/water. Yield 7 g, melting point 68-69° C.

Example 3

Ethyl 1-methyl-3-difluoromethyl-5-fluoro-1H-pyrazole-4-carboxylate

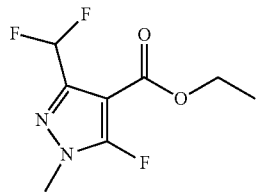

In an autoclave 10.5 g of Ethyl 1-methyl-3-chlorodifluoromethyl-5-fluoro-1H-pyrazole-4-carboxylate in 100 ml of THF, 6 g Potassium carbonate and 150 mg Pd(OH)2 on carbon support were added. The autoclave was flushed with nitrogen and pressurised to 15 bar hydrogen. Reaction mixture in autoclave was stirred at 100° C. for 6 h. After filtration of the catalyst, the solvent was removed under reduced pressure and the product was obtained as a solid and purified via crystallization from mixture isopropanol/water. Yield 7.2 g.

The invention claimed is:

1. Process for preparing 1-alkyl-3-difluoromethyl-5-fluor-1H-pyrazole-4-carbaldehydes or esters thereof of formula (I)

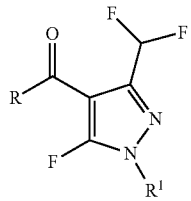

wherein $R^1$ is $C_1$-$C_6$-alkyl and R is H or $C_1$-$C_6$-alkoxy, characterized in that
5-fluoro-1-alkyl-3-chlorodifluoromethyl-5-fluoro-1H-pyrazole-4-carbaldehydes or esters thereof of formula (II)

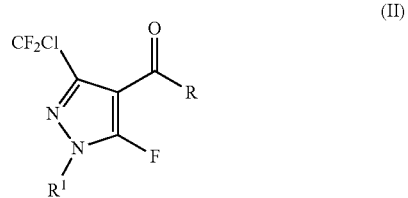

wherein R and $R^1$ are as stated above,
is reacted by means of catalytic hydrogenation.

2. The process according to claim 1 wherein $R^1$ is methyl, ethyl, n-propyl, isopropyl, butyl or pentyl.

3. The process according to claim 2 wherein $R^1$ is methyl or ethyl.

4. The process according to claim 3 wherein $R^1$ is methyl.

5. The process according to claim 1 wherein the catalytic hydrogenation is done in presence of a base.

6. The process according to claim 5 wherein the base is sodium carbonate, potassium carbonate, sodium bicarbonate, potassium bicarbonate, mono-, di- or trisodium phosphate, tripotassium phosphate, sodium hydroxide, potassium hydroxide, triethylamine, tributylamine, diazabicycloundecene (DBU), diazabicyclononene (DBN), pyridine, lutidine, 2-, 3- or 4-picoline or diazabicyclooctane (DABCO).

7. The process according to claim 5 wherein the base is triethylamine.

* * * * *